(12) United States Patent
Klein et al.

(10) Patent No.: US 8,823,535 B2
(45) Date of Patent: Sep. 2, 2014

(54) EARLY DETECTION OF ENVIRONMENTAL CONDITIONS THAT WILL LEAD TO CREEP CORROSION ON PRINTED CIRCUIT BOARDS IN DATA CENTERS

(71) Applicant: International Business Machines Corporation, Armonk, NY (US)

(72) Inventors: Levente Klein, Tuckahoe, NY (US); Prabjit Singh, Poughkeepsie, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 75 days.

(21) Appl. No.: 13/705,224

(22) Filed: Dec. 5, 2012

(65) Prior Publication Data

US 2014/0152449 A1    Jun. 5, 2014

(51) Int. Cl.
*G08B 21/00* (2006.01)

(52) U.S. Cl.
USPC ......... 340/662; 324/700; 204/404; 205/775.5

(58) Field of Classification Search
USPC ............ 340/662, 636.19; 324/71.1, 700, 691; 204/404; 205/775.5
See application file for complete search history.

(56) References Cited

U.S. PATENT DOCUMENTS

| 5,286,357 | A | 2/1994 | Smart et al. |
| 6,997,043 | B2 | 2/2006 | Swanson et al. |
| 8,149,004 | B2 * | 4/2012 | Raju et al. ..................... 324/700 |
| 2009/0039864 | A1 * | 2/2009 | Gordon ........................ 324/71.1 |

FOREIGN PATENT DOCUMENTS

| CN | 2466634 | 12/2001 |
| CN | 201210135695 | 8/2012 |
| DE | 201012102836 | 10/2012 |
| EP | 2339325 | 6/2011 |
| JP | 2005207813 | 8/2005 |
| JP | 2007225546 | 9/2007 |
| JP | 2009236524 | 10/2009 |

* cited by examiner

*Primary Examiner* — Toan N Pham
(74) *Attorney, Agent, or Firm* — Margaret A. McNamara (57) ABSTRACT

Apparatus and method for directly detecting the atmospheric conditions leading to creep corrosion of printed circuit boards (PCBs) well before the PCBs in the computers start suffering from creep corrosion. The embodiment indicates the propensity of the air towards creep corrosion on PCBs. Additionally, to avoid the false reading due to condensed moisture, condensed moisture may be avoided by using a heater attached to the creep corrosion monitor that keeps the creep corrosion monitor above the dew point temperature.

19 Claims, 6 Drawing Sheets

EARLY DETECTION OF ENVIRONMENTAL CONDITIONS THAT WILL LEAD TO CREEP CORROSION ON PRINTED CIRCUIT BOARDS IN DATA CENTERS

BACKGROUND OF THE INVENTION

1. Field of the Invention

Creep corrosion is the corrosion of copper and silver metallization on printed circuit boards (PCBs) and the subsequent creep (migration) of the sulfide corrosion products across the PCB surface, thereby, electrically shorting neighboring circuit board features and causing the electronic device to malfunction.

2. Description of the Related Art

High levels of sulfur-bearing gaseous contamination along with the synergistic effects of humidity and other contaminants such as ozone and nitrogen dioxide can cause creep corrosion on printed circuit boards.

The contamination in the air can be measured by chemical analysis or by reactive monitoring. Chemical analysis of the air can determine the composition of the air including many of its contaminants such as sulfur-bearing gases. Reactive monitoring measures the corrosion rates of copper and silver coupons (metal foils) exposed to air. Reactive monitoring does not measure the composition of the air. It does give some information about the contaminants in the air. For example, if the corrosion product consists of a thick layer of sulfide, it can be readily concluded that the air is high in sulfur-bearing contaminants. But neither of these methods gives any direct indication of whether the contamination levels are severe enough to cause creep corrosion, which is a common mode of electronic hardware failure in environments high in sulfur-bearing gases.

There is a need for a device that will directly detect the presence of atmospheric conditions leading to creep corrosion of PCBs well before the PCBs in the computers start suffering from creep corrosion.

SUMMARY OF THE INVENTION

The invention describes a device that directly detects the atmospheric conditions leading to creep corrosion of PCBs well before the PCBs in the computers start suffering from creep corrosion. The invention indicates the propensity of the air towards creep corrosion on PCBs.

In one aspect of the invention, an apparatus to monitor environmental conditions that may lead to creep corrosion is provided. The apparatus includes: a printed circuit board with inter-digitated comb patterns having spacing in between the patterns; a printed circuit board with a controlled level of organic acid flux contamination dried on the surface at the temperature of solder reflow; a power supply and a high resistance resistor connected to the printed circuit board in series; a microprocessor connected across the high resistance resistor for monitoring changes in resistance of the circuit; and an alarm connected to the microprocessor wherein the alarm is activated when voltage in the circuit exceeds a threshold value.

In another aspect of the invention, a method to monitor creep corrosion propensity of the air is provided. The method includes: providing a printed circuit board with inter-digitated comb patterns having spacing in between the patterns, the circuit board connected to a microprocessor; connecting, in series, a power supply and a high resistance resistor to the printed circuit board connecting at least one of a data logger and an alarm circuit to the microprocessor to create a corrosion monitor; monitoring, by the microprocessor, the resistance of the circuit as voltage passes through the circuit; and writing data to the data logger and triggering the alarm circuit in response to the voltage exceeding a threshold value.

DETAILED DESCRIPTION OF THE PREFERRED EMBODIMENT

In an embodiment, a circuit is created with a 10 V power source in series with a 100 k-Ohm resistor and printed circuit board (PCB) having an inter-digitated comb pattern. Current leakage is measured between the patterns. A data logger is connected across the resistor along with an alarm. The data logger can store the voltage as a function of time. The alarm can be set to go off when the voltage across the 100 k-Ohm resistor goes above 1 V. The data logger stores the voltage versus time information, wherein the information includes the history of level of contaminants in the air that can cause creep corrosion. If the voltage values are zero to very low, the data center air is clean and does not cause creep corrosion on the circuit board. If the voltage values rise to high values in the 1 V range, it means that the air in the data center has high propensity towards creep corrosion.

If there is a short circuit between the inter-digitated comb patterns, current will flow from the power source through the resistor and the corrosion product short circuiting the comb patterns. A creep corrosion event will be observed as high leakage current between the patterns on the test board. The high leakage current will trigger an alarm connected to the circuit that the air contamination is above the critical level for creep corrosion. The creep corrosion monitor should be hung in the vicinity of the hardware that needs to be protected from creep corrosion due to the corrosive gases. In a preferred embodiment, the creep corrosion monitor is located in front of the computer rack on the air intake side to make sure that the monitor is subject to the air entering the computer.

If the atmospheric conditions in the data center are severe enough to cause creep corrosion, creep corrosion will occur first on this test PCB, well before it will occur on the actual hardware, because the test PCB contains silver metallization and an organic acid flux contamination, which in combination are known to have the highest propensity to creep corrosion of all known PCB assembly technologies in use today.

The high leakage current will raise the voltage across the 100 k-Ohm resistor. The voltage versus time data will be stored in the data logger for later retrieval. The alarm is set to go off if the voltage rises above 1 V. The triggering of the alarm will indicate that creep corrosion has occurred on the test PCB and short circuited the comb patterns. Therefore the air in the data center is contaminated above the critical level for creep corrosion.

If the alarm goes off, the comb pattern has become electrically shorted. The comb pattern test PCB should be replaced.

For ease of replacement, the comb pattern test PCB can be such that it can be unplugged and a new test PCB plugged into the circuit with ease.

The spacing and the width of the inter-digitated comb patterns can be varied over a large range. So can the values of the power source voltage, the resistor and the voltage at which the alarm should be triggered. If the atmospheric conditions in the data center are severe enough to cause creep corrosion, then creep corrosion will occur first on this test circuit boards, well before it will occur on the actual hardware, because the test circuit an organic acid flux contamination.

Figure 1:
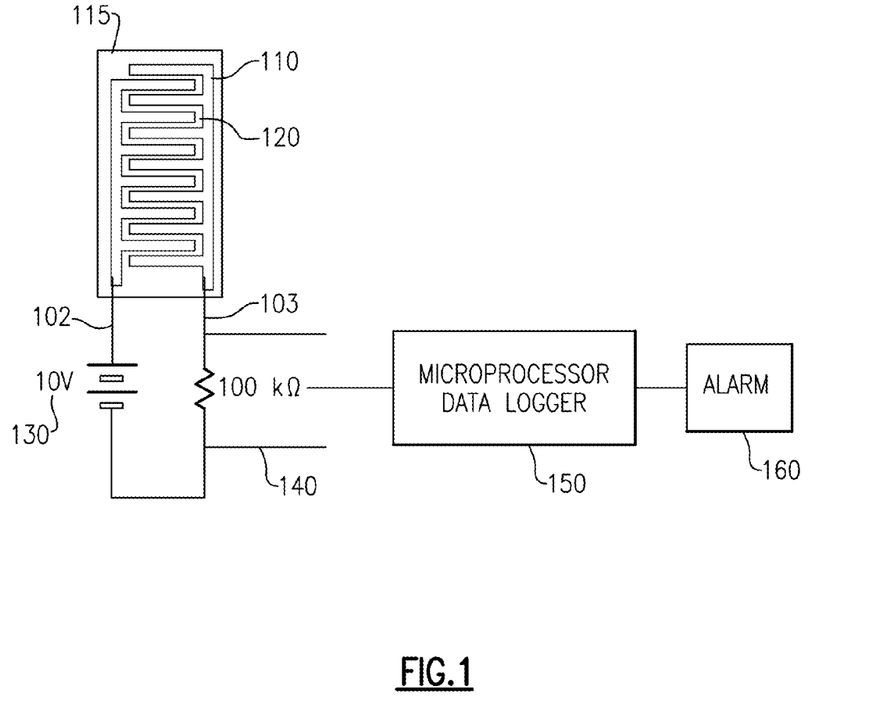
FIG. 1: depicts a creep corrosion sensor

With regards now to FIG. 1, inter-digitated comb patterns 110 are printed on a printed circuit board (PCB) 115 using the standard materials and processes used to fabricate current PCBs. The comb patterns may be made of copper or a copper alloy such as copper plated with silver. For example, the PCB may be patterned with inter-digitated copper metallization that is over-plated with silver 1-10 micro-meters thick. The spacing 120 between the comb patterns may be small, about 0.25 mm. The width of the lines may be about 1 mm. Wires 102 and 103 are soldered to the inter-digitated comb patterns. An aggressive organic acid soldering flux, preferably a no-clean flux (because that is the most aggressive flux being used today), is sprayed on the pattern, so that the contamination on the pattern is 10-100 microgram NaCl equivalent per cm square. The fluxed PCB may be baked at about 200 deg C. for a few minutes to dry the flux.

10V from a power source 130 is applied across the combs with a resistor (in this example, 100 k-Ohm) 140 in series. When the creep corrosion occurs short circuiting the combs to less than a 1 mega-Ohms leakage path, the voltage across the 100 k-Ohms resistor 140 will rise to 0.9V. When the microprocessor/data logger 150 detects more than 1V across the 100K-Ohm resistor it triggers an alarm 160 indicating that creep corrosion has occurred on the creep corrosion monitor.

In a preferred embodiment, when the leakage current goes above 10 micro amperes, the output voltage goes above 1V to trigger the alarm. 10 micro ampere at 10V amounts to 1 mega-Ohm resistance of the sensor. So it is desired to trigger the alarm when the sensor resistance goes below 1 mega Ohm.

Figure 2:
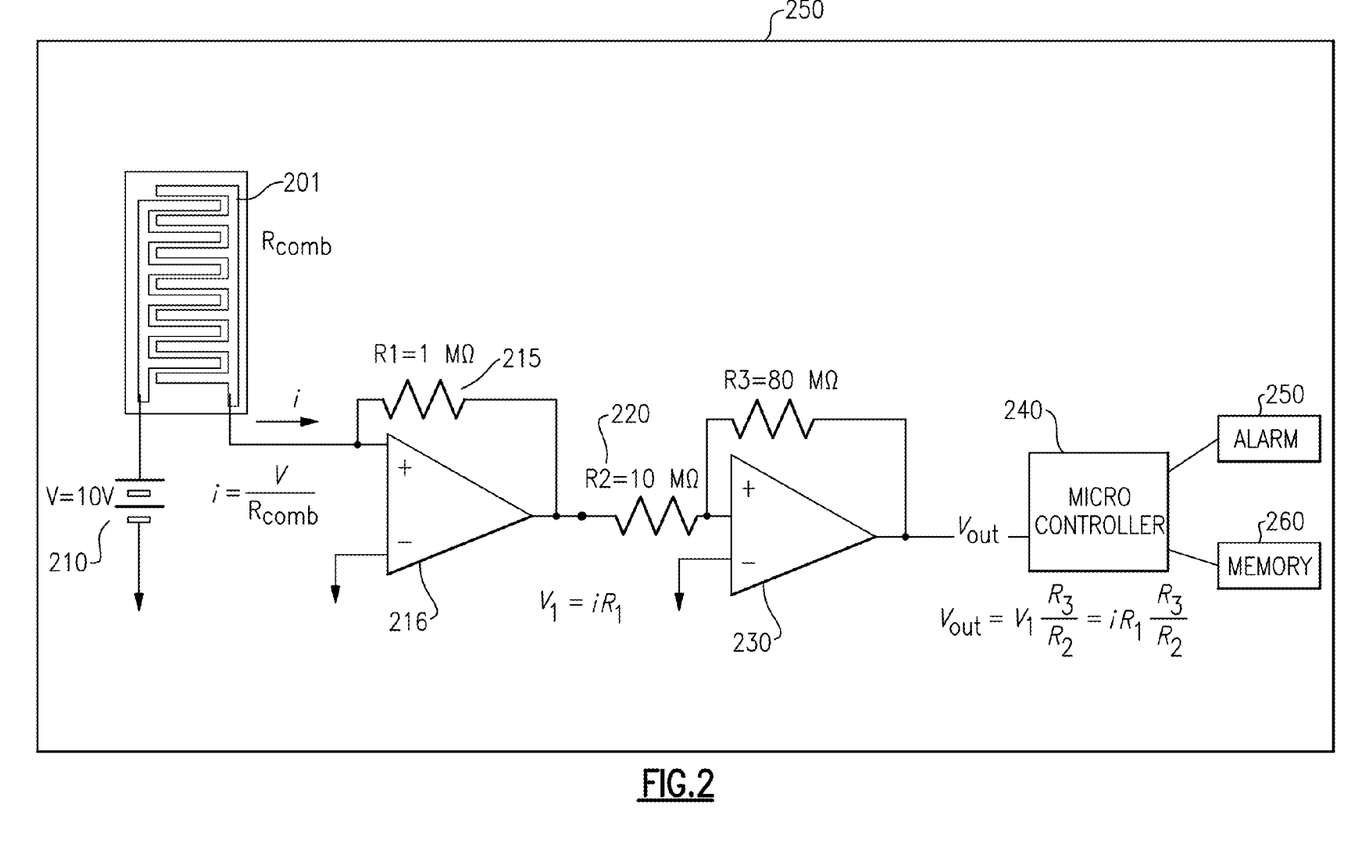
FIG. 2: depicts a circuit diagram of a creep corrosion sensor

In another embodiment, to be able to detect small current reliably a double stage amplification based on two operational amplifiers is used. Turning now to FIG. 2, voltage source 210 is connected to the two inter-digitated comb patterns 201. The voltage source may be a 10Vdc battery. The current that flows through the circuit is determined by the comb structure that becomes conductive when the relative humidity rises above a certain value or creep corrosion bridges the gap between the interdigitated combs. A high resistance (about 1 mega-Ohm) resistor 215 is connected in series. Voltage across the 1 mega-Ohm resistor provides a measure of the leakage current across the inter-digitated comb patterns. If the environmental condition leads to creep corrosion bridging the gap between the interdigitated combs or if moisture has condensed on the PCB surface a small current flowing between the two electrodes will be detected. Since the resistance of the comb 201 is larger than 1 Giga ohm the current would be very small. If the humidity increases to cause condensation or creep corrosion bridges the gap between the interdigitated combs, the resistance will decrease in to the mega-Ohm range. Overall these would be small currents that are difficult to measure in the field. The current would be the voltage divided by the resistance of the comb structure. The hardware consisting of the battery, the resistor and the comb pattern, all electrically connected in series and mounted and housed in a chassis 250 with generous perforated openings so that air has easy access to and can flow freely over the PCB surface.

The first op amp (transimpedance amplifier) 216 amplifies the current that flows across the comb structure and convert it to voltage as shown by the equation $V1=iR1$.

The current is amplified in first stage 220 (as the resistance of the inter digitated electrode under corrosive conditions is expected to be –1 mega-Ohm). The second operational amplifier amplifies the voltage in the second stage 230. The gain of the opamp is calculated by (R3/R2). In this example, since V is 10 volts, R1=1 mega-Ohm, R2=10 mega-Ohm and R3=80 mega-Ohm, Vout is 8V. The circuit may be connected to a microcontroller 240. Microcontroller 240 may be connected to an alarm 250 which may provide an alert that conditions for creep corrosion exist. The alarm may be an audio or visual alert, or an electronic message. The microcontroller may also be connected to a memory 260 and perform data logging and analysis.

If the environmental condition has not caused to creep corrosion to bridge the gap between the inter-digitated combs or moisture has not condensed on the PCB surface, the resistance of the inter-digitated electrode is expected to be >100; no signal will be detected.

The choice for resistor are representative values and they can be changed according to the desired resolution of the storage device In another embodiment, the temperature of the creep corrosion monitor is kept above the dew point to avoid condensation and a false positive that creep corrosion has occurred, when in fact only condensation has occurred. If the humidity becomes so high that the dew point temperature is higher than the temperature of the creep corrosion sensor, moisture will condense on the creep corrosion sensor. The moisture bridging the gap will make the gap between the combs electrically conductive giving a false indication that creep corrosion has occurred.

To avoid the false reading due to condensed moisture, condensed moisture is avoided using a heater attached to the creep corrosion monitor that keeps the creep corrosion monitor above the dew point temperature.

Figure 3:
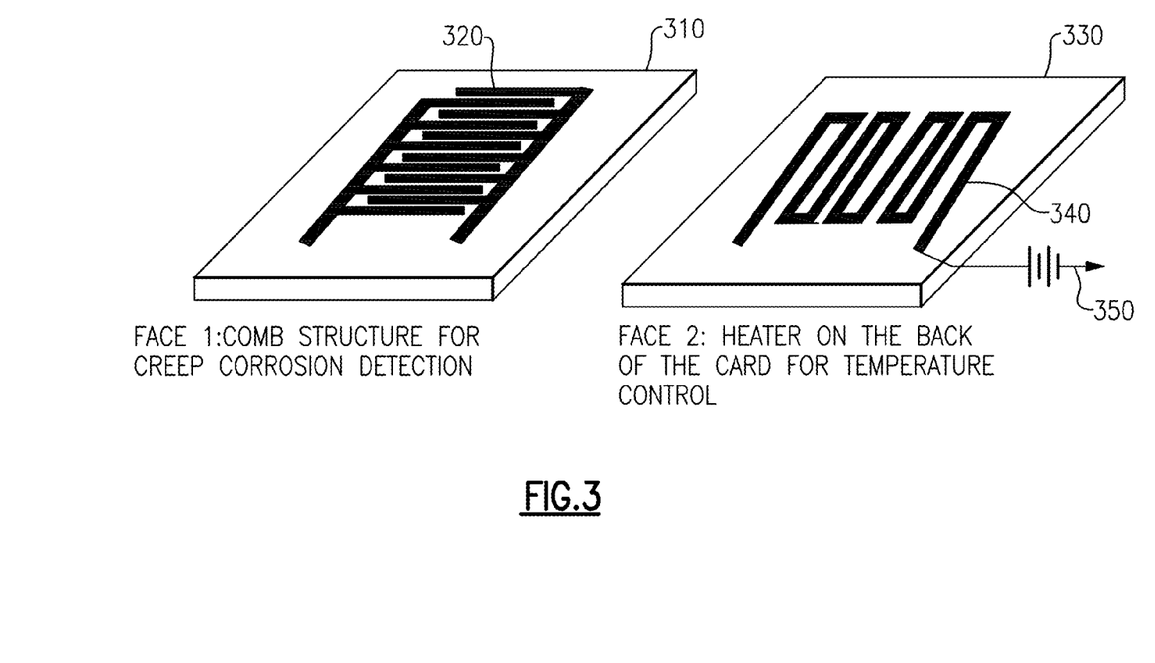
FIG. 3: depicts the front and back sides of a printed circuit board having a sensor on one side and a heater on the other side

FIG. 3 shows a printed circuit board 310 with a creep corrosion sensor 320 and heater 320. 330 depicts the underside of the circuit board with a heater 340 attached. The heater may be connected to a separate voltage source 350 and changing the voltage may adjust the temperature.

The dew point can be calculated if the temperature and relative humidity are known. There are multiple approximation but the most widely used one is the Magnus formula as mentioned in http://journals.ametsoc.org/doi/pdf/10.1175/BAMS-86-2-225

The heater would be positioned on the bottom face of the PCB card while the comb structure/coupon would be on the front face of the PCB card. The heater can be serpentine made of copper similar to the comb structure and will resistively heat up as a current is passed through. The heater would be connected to a voltage source Normally the comb structure can show a conduction either if there is copper creep corrosion or if there is a water layer that bridges the gap between the two combs. Heating the structure with the comb will eliminate the water bridge and if the resistance is still low then it will be likely due to copper creep corrosion.

Figure 4:
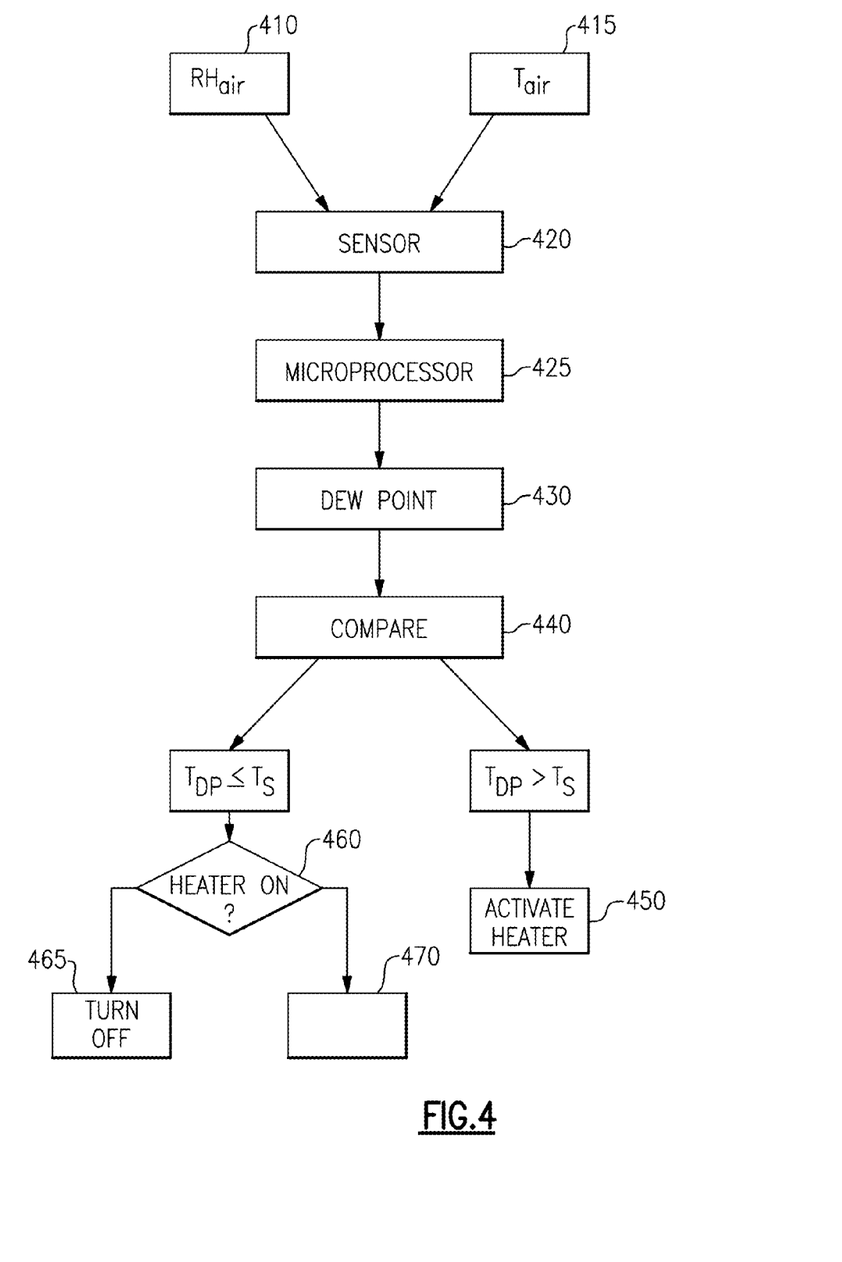
FIG. 4: depicts a flowchart for activating the heater

With regards to FIG. 4, air temperature 415 and relative humidity 410 are read by sensor 420 to provide data to microcontroller 425 to calculate dew point temperature 430.

Microcontroller 425 is connected to the creep corrosion monitor and records the temperature 435 of the creep corrosion monitor.

In 440, dew point temperature 430 is compared with the temperature of the creep corrosion monitor 435. If the dew point temperature 430 is greater than temperature of the creep corrosion monitor 435, the heater is turned on as shown in 450.

If the temperature of the creep corrosion monitor is equal or greater than the dew point, the microcontroller will check if the heater is on in 460. If the heater is on, the microcontroller will send a signal to turn off the heater as in step 465. If the heater is not on, the microcontroller does not send a signal and leaves the heater off 470.

Figure 5:
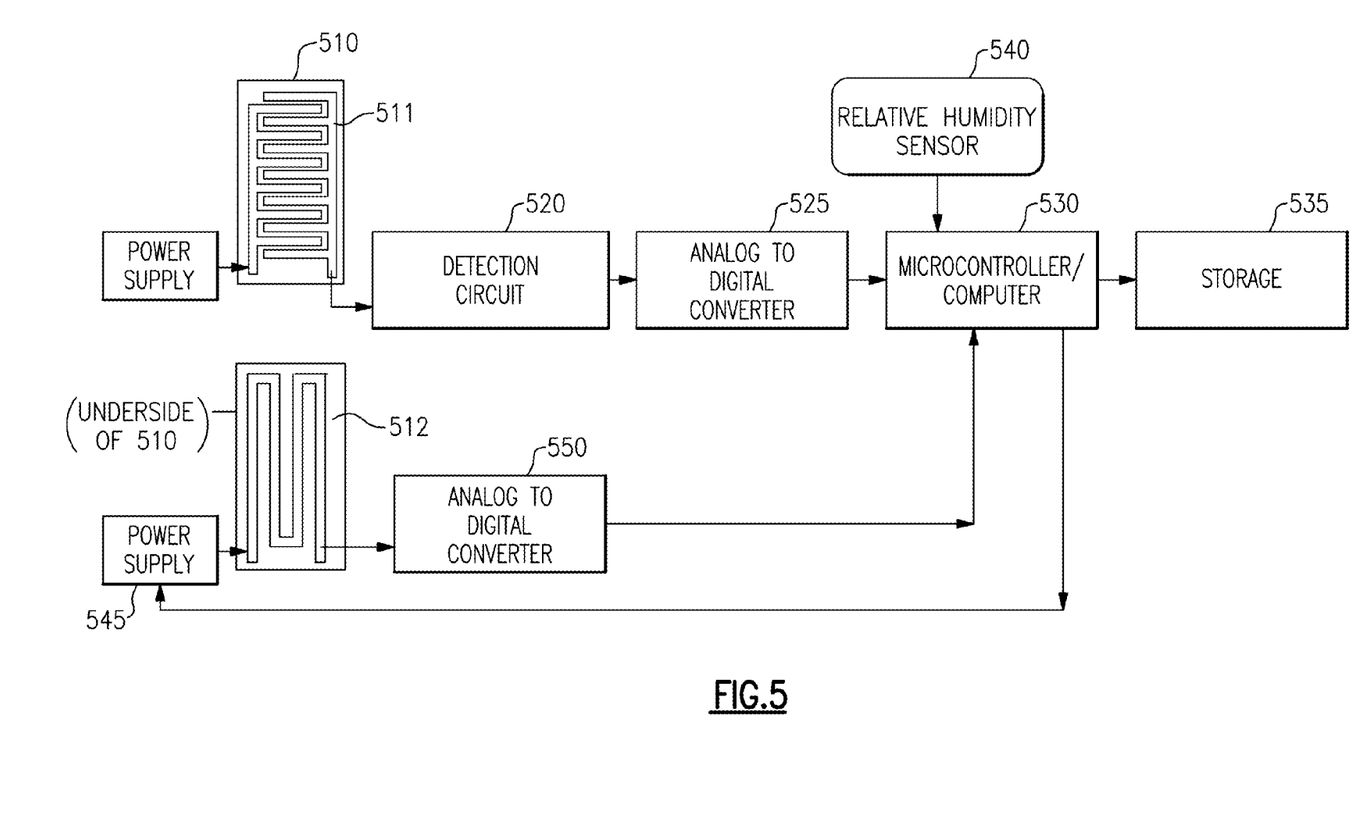
FIG. 5: depicts a high level view of the sensor and heater

FIG. 5 is another depiction of an embodiment showing a printed circuit board 510 with a creep corrosion sensor 511. The underside of 510 is attached to a heater 512. Sensor 511 is attached to a detection circuit 520 as discussed earlier in FIG. 2. The detection circuit is connected to an analog to digital converter 525 which converts analog data to digital format. The data is then transferred to microcontroller 530. Microcontroller 530 may be attached to a storage device 535.

Microcontroller 530 is attached to sensor 540 which records environmental conditions such as air temperature and relative humidity. 530 regulates power supply 545 to control heater 512. The heater 512 is attached to analog to digital converter 550 which converts data so that it can be fed back to 530 to provide continuous monitoring and adjustment of the heater in response to changing environmental conditions.

Figure 6:
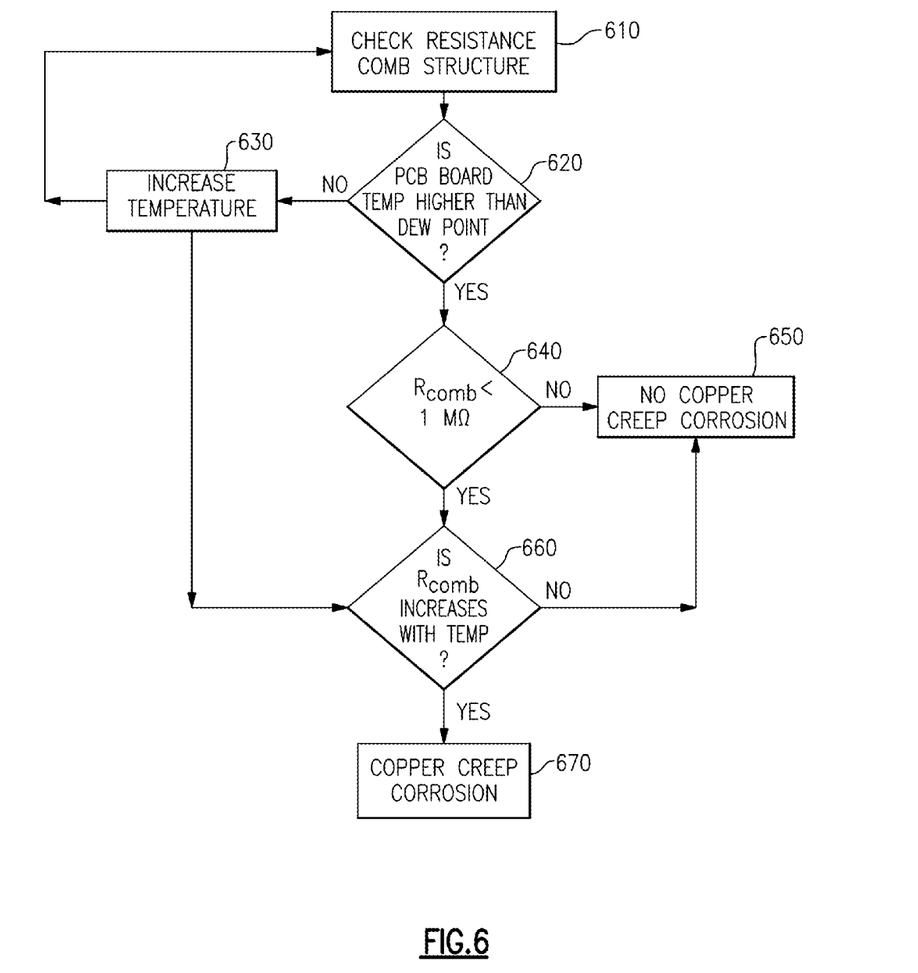
FIG. 6: depicts a flowchart for determining the existence of creep corrosion

FIG. 6 depicts a flowchart diagram of the microprocessor routine. In an embodiment, the Corrosion Sensor sends output data into the microprocessor. In 610 the microcontroller reads the resistance of the comb structure and determines in 620 whether the PCB board temperature is higher than the dew point. If it is not, a signal is sent to increase the temperature in 630 of the comb structure by, for example, activating the heater and the microprocessor continues to monitor resistance of the comb structure. If the PCB board temperature is higher than the dew point, the microcontroller then determines if the resistance of the comb structure is below a threshold resistance 640. In this example, the threshold is 1 Mega-Ohm. If resistance of the comb is not less than 1 MOHM, then the microcontroller will not indicate evidence of copper creep corrosion. If resistance of the comb is greater than 1 MOhm, the microprocessor monitors the resistance of the comb to determine if the resistance is increasing as the temperature increases 660. If yes, then there is evidence of copper creep corrosion and the microprocessor may trigger an alarm. If resistance of the comb structure does not increase with temperature, then microprocessor will not indicate evidence of copper creep corrosion 650.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to explain the principles of the invention and the practical application, and to enable others of ordinary skill in the art to understand the invention through various embodiments and the various modifications thereto which are dependent on the particular use contemplated.

We claim:

1. An apparatus to monitor environmental conditions that may lead to creep corrosion, the apparatus comprising:
   a printed circuit board with inter-digitated comb patterns having spacing in between the patterns and a controlled level of organic acid flux contamination;
   a power supply and a high resistance resistor connected to the printed circuit board in series;
   a microprocessor connected across the high resistance resistor for monitoring changes in resistance of the circuit; and
   an alarm connected to the microprocessor wherein the alarm is activated when voltage in the circuit exceeds a threshold value.

2. The apparatus of claim 1 wherein the inter-digitated comb patterns are made of a copper containing material.

3. The apparatus of claim 1 wherein spacing between the patterns is about 0.25 mm.

4. The apparatus of claim 1, wherein the alarm circuit indicates the creep corrosion propensity of air.

5. The system of claim 1 wherein the alarm circuit triggers the alarm when a test PCB short circuits which indicates that creep corrosion has occurred on the PCB.

6. The apparatus of claim 1 further comprising a data logger connected to a non-transitory storage medium for storing voltage versus time information, wherein the information includes a history of level of contaminants in air that can cause creep corrosion.

7. The apparatus of claim 1 wherein the flux contamination on the pattern is 10 to 100 microgram NaCl equivalent per cm square.

8. The apparatus of claim 1 further comprising a sensor for monitoring relative humidity.

9. The apparatus of claim 1 further comprising a heater connected to the creep corrosion monitor wherein the microprocessor controls the heater based on relative humidity and resistance of the circuit.

10. The apparatus of claim 9 wherein the heater is connected to a separate power supply from the creep corrosion monitor.

11. The method of claim 1 wherein the Inter-digitated comb patterns are made of a copper containing material.

12. The method of claim 1 wherein the printed circuit board is attached to a heater, said heater controlled by the microprocessor.

13. The method of claim 12 further comprising monitoring, by the microprocessor, a temperature of the printed circuit board.

14. The method of claim 13 wherein a sensor is connected to the microprocessor to enable the microprocessor to calculate dew point.

15. The method of claim 14 further comprising controlling the heater based on a comparison between the dew point and the temperature of the printed circuit board.

16. The method of claim 1 further comprising triggering, by the circuit, an alarm when a test PCB short circuits indicating that creep corrosion has occurred on the PCB.

17. The method of claim 1 further comprising storing, by a data logger, voltage versus time information, wherein the information includes a history of level of contaminants in air that can cause creep corrosion.

18. The method of claim 1 wherein the flux is an aggressive organic acid soldering no-clean flux.

19. A method to monitor creep corrosion propensity of air comprising:
   providing a printed circuit board with inter-digitated comb patterns having spacing in between the patterns, the circuit board connected to a microprocessor; connecting, in series, a power supply and a high resistance resistor to the printed circuit board connecting at least one of a data logger and an alarm circuit to the microprocessor to create a corrosion monitor; monitoring, by the microprocessor, a resistance of the circuit as voltage passes through the circuit; writing data to the data logger and triggering the alarm circuit in response to the voltage exceeding a threshold value.

\* \* \* \* \*